United States Patent
Conklin et al.

(10) Patent No.: US 10,751,174 B2
(45) Date of Patent: *Aug. 25, 2020

(54) LIMITED EXPANSION HEART VALVE

(71) Applicant: Edwards Lifesciences Corporation, Irvine, CA (US)

(72) Inventors: Brian S. Conklin, Orange, CA (US); Da-Yu Chang, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/141,604

(22) Filed: Sep. 25, 2018

(65) Prior Publication Data

US 2019/0021854 A1  Jan. 24, 2019

Related U.S. Application Data (63) Continuation of application No. 15/260,053, filed on Sep. 8, 2016, now Pat. No. 10,080,653.

(60) Provisional application No. 62/216,936, filed on Sep. 10, 2015.

(51) Int. Cl.
*A61F 2/24* (2006.01)

(52) U.S. Cl.
CPC .......... *A61F 2/2418* (2013.01); *A61F 2/2409* (2013.01); *A61F 2220/0033* (2013.01); *A61F 2220/0075* (2013.01)

(58) Field of Classification Search
CPC ......... A61F 2/24; A61F 2/2418; A61F 2/2412

USPC ................................................. 623/2.1–2.19
See application file for complete search history.

(56) References Cited

U.S. PATENT DOCUMENTS

| | | |
|---|---|---|
| 3,143,742 A | 8/1964 | Cromie |
| 3,320,972 A | 5/1967 | High et al. |
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |

(Continued)

FOREIGN PATENT DOCUMENTS

| | | |
|---|---|---|
| EP | 0125393 A1 | 11/1984 |
| EP | 0143246 A2 | 6/1985 |

(Continued)

*Primary Examiner* — Suzette J Gherbi
(74) *Attorney, Agent, or Firm* — Guy Cumberbatch (57) ABSTRACT

A prosthetic heart valve configured to replace a native heart valve and having a support frame configured to be reshaped into an expanded form in order to receive and/or support an expandable prosthetic heart valve therein is disclosed, together with methods of using same. Interlocking members or flexible loops are included to limit expansion of the valve to one or two valve sizes, for example, with a 2-mm gap between each valve size. The valve may include an internal structural band with overlapped free ends having structure for limiting expansion, or external loops of suture may be added to the fabric covering which limits expansion.

21 Claims, 6 Drawing Sheets

(56) References Cited

U.S. PATENT DOCUMENTS

| | | |
|---|---|---|
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,687,463 A | 6/1987 | Fisher et al. |
| 4,680,031 A | 7/1987 | Alonso |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,762 A | 5/1998 | Love et al. |
| 5,766,240 A | 6/1998 | Johnson |
| 5,800,527 A * | 9/1998 | Jansen ............... A61F 2/2409 623/2.38 |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,110,200 A | 6/2000 | Hinnenkamp |
| 6,083,179 A | 7/2000 | Oredsson |
| 6,099,475 A | 8/2000 | Seward et al. |
| 6,106,550 A | 8/2000 | Magovern et al. |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson, IV et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,761,736 B1 * | 7/2004 | Woo ............... A61L 33/025 623/1.46 |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |

(56) References Cited

U.S. PATENT DOCUMENTS

| | | |
|---|---|---|
| 6,893,459 B1 | 5/2005 | Macoviak |
| 6,893,460 B2 | 5/2005 | Spenser et al. |
| 6,908,461 B2 | 6/2005 | Cribier |
| 6,939,365 B1 | 9/2005 | Fogarty et al. |
| 7,011,681 B2 | 3/2006 | Vesely |
| 7,025,780 B2 | 4/2006 | Gabbay |
| 7,070,616 B2 | 7/2006 | Majercak et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,632,309 B1 * | 12/2009 | Brendzel ............... A61F 2/0077 623/2.42 |
| 7,998,151 B2 | 8/2011 | St. Goar et al. |
| 9,504,566 B2 * | 11/2016 | Guttenberg ........... A61F 2/2409 |
| 9,675,453 B2 * | 6/2017 | Guttenberg ........... A61F 2/2409 |
| 10,080,653 B2 * | 9/2018 | Conklin ................ A61F 2/2418 |
| 10,226,331 B2 * | 3/2019 | Lane ..................... A61F 2/2409 |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0093147 A1 * | 5/2003 | Ogle ....................... A61L 15/32 623/2.12 |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulia et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Saiahieh et al. |
| 2005/0137688 A1 | 6/2005 | Saiahieh et al. |
| 2005/0137690 A1 | 6/2005 | Salahieh et al. |
| 2005/0137692 A1 | 6/2005 | Haug et al. |
| 2005/0137695 A1 | 6/2005 | Saiahieh et al. |
| 2005/0159611 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Saiahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulia et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0185565 A1 | 6/2007 | Schwammenthal et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0198097 A1 | 8/2007 | Zegdi |

(56) References Cited

U.S. PATENT DOCUMENTS

| | | |
|---|---|---|
| 2007/0203575 A1 | 8/2007 | Forster et al. |
| 2007/0203576 A1 | 8/2007 | Lee et al. |
| 2007/0213613 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0192599 A1 | 7/2009 | Lane et al. |
| 2010/0049313 A1 | 2/2010 | Alon et al. |
| 2010/0145438 A1 | 6/2010 | Barone |
| 2010/0256723 A1 | 10/2010 | Murray |
| 2010/0331972 A1 | 12/2010 | Pintor et al. |
| 2014/0128964 A1 | 5/2014 | Delaloye |
| 2014/0188219 A1 | 7/2014 | Conklin et al. |
| 2014/0188221 A1 | 7/2014 | Chung et al. |
| 2015/0366664 A1* | 12/2015 | Guttenberg ............ A61F 2/2409 623/2.17 |
| 2016/0324631 A1* | 11/2016 | Lane ..................... A61F 2/2409 |
| 2016/0367365 A1* | 12/2016 | Conklin ................ A61F 2/24 |
| 2017/0000603 A1* | 1/2017 | Conklin ................ A61F 2/2418 |
| 2017/0000604 A1* | 1/2017 | Conklin ................ A61F 2/2409 |
| 2017/0231764 A1* | 8/2017 | Morin .................. A61F 2/2418 623/2.11 |
| 2017/0281342 A1* | 10/2017 | Chung .................. A61F 2/2418 |

FOREIGN PATENT DOCUMENTS

| | | |
|---|---|---|
| SU | 1116573 A1 | 7/1985 |
| SU | 1697790 A1 | 12/1991 |
| WO | 9213502 A1 | 8/1992 |
| WO | 9742871 A1 | 11/1997 |

\* cited by examiner

LIMITED EXPANSION HEART VALVE

CROSS REFERENCE TO RELATED APPLICATIONS

This application is a continuation of U.S. patent application Ser. No. 15/260,053, filed Sep. 8, 2016, now U.S. Pat. No. 10,080,653, which claims the benefit of U.S. Patent Application No. 62/216,936, filed Sep. 10, 2015, the entire contents all of which are expressly incorporated by reference herein.

TECHNICAL FIELD

The present disclosure relates to a heart valve for heart valve replacement, and more particularly to modifications to the construction of a surgical heart valve to enable receiving an expandable prosthetic heart valve therein and to expand to a limited degree.

BACKGROUND

The heart is a hollow muscular organ having four pumping chambers separated by four heart valves: aortic, mitral (or bicuspid), tricuspid, and pulmonary. Each heart valve is comprised of a dense fibrous ring known as the annulus, and leaflets or cusps attached to the annulus.

Heart valve disease is a widespread condition in which one or more of the valves of the heart fails to function properly. In a traditional valve replacement operation, the damaged leaflets are typically excised and the annulus sculpted to receive a replacement prosthetic valve.

In tissue-type valves, a whole xenograft valve (e.g., porcine) or a plurality of xenograft leaflets (e.g., bovine pericardium) can provide fluid occluding surfaces. Synthetic leaflets have been proposed, and thus the term "flexible leaflet valve" refers to both natural and artificial "tissue-type" valves. In typical surgical heart valves, two or more flexible leaflets are mounted within a peripheral support structure that usually includes posts or commissures extending in the outflow direction to mimic natural fibrous commissures in the native annulus. The metallic or polymeric "support frame," sometimes called a "wireform" or "stent," has a plurality (typically three) of large radius cusps supporting the cusp region of the flexible leaflets (e.g., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. Components of the valve are usually assembled with one or more biocompatible fabric (e.g., DACRON® polyethylene terephthalate) coverings, and a fabric-covered sewing ring is provided on the inflow end of the peripheral support structure.

Sometimes the need for complete valve replacement may arise after a patient has already had an earlier valve replacement. For example, a prosthetic surgical heart valve that was successfully implanted to replace a native valve may itself suffer damage and/or wear and tear many years after initially being implanted. Implanting a new prosthetic heart valve directly within a previously-implanted prosthetic heart valve (a so-called valve-in-valve procedure) may be impractical since traditional prosthetic surgical heart valves may not be configured to easily receive such a valve-within-a-valve implantation in a manner which provides secure seating for the new valve while also having a large enough annulus within the new valve to support proper blood flow therethrough. Namely, conventional surgical valves have a relatively stable diameter that is not intended to be compressed or expanded during delivery, and after implant when functioning as a one-way valve.

Some attention has been paid to the problem of implanting a new valve within an old valve. In particular, the following disclose various solutions for valve-in-valve systems: U.S. Pat. No. 8,613,765, filed Jul. 7, 2011; U.S. Pat. No. 9,314,335, filed Sep. 19, 2008; U.S. Pat. No. 9,364,322, filed Dec. 20, 2013; U.S. Pat. No. 9,375,310, filed Dec. 20, 2013; and International Patent Publication No. WO 2012/018779, filed Aug. 2, 2011. The entire disclosures of these publications are expressly incorporated herein by reference.

Despite certain advances in the valve-in-valve area, there remains a need for a prosthetic heart valve which facilitates valve-in-valve procedures and simplifies manufacturing techniques.

SUMMARY OF THE INVENTION

Some embodiments provide a prosthetic surgical heart valve configured to receive a second prosthetic heart valve therein, such as a catheter-deployed (transcatheter) prosthetic heart valve. The surgical heart valves are adapted for post-implant expansion and expansion limiters that prevent over-expansion.

The present application provides a number of embodiments of prosthetic surgical heart valves adapted for post-implant expansion each defining an inflow end and an outflow end and comprise a valve member including a non-collapsible inner structural support stent having three upstanding commissure posts extending in an outflow direction and spaced evenly around a periphery of the support stent alternating with three arcuate inflow cusps midway between adjacent commissure posts. Three flexible leaflets attach along the commissure posts and inflow cusps of the support stent and are configured to ensure one-way blood flow through the valve member. The support stent periphery defined a non-collapsible delivery and implant circumference having a first diameter, wherein the support stent permits expansion of the periphery from the first diameter to a second diameter larger than the first diameter upon application of an outward dilatory force from within the support stent substantially larger than forces associated with normal physiological use. The support stent includes a structural band extending around the periphery that permits expansion of the support stent.

In a first embodiment, the structural band has overlapping free ends such that relative sliding of the overlapping free ends permits expansion of the support stent, and the valve member includes an expansion limiting spacer interposed between the overlapping free ends that engages both free ends and prevents over-expansion of the stent past the second diameter. Desirably, the overlapping free ends are located at a single one of the inflow cusps of the support stent. The expansion limiting spacer may have two fingers that are radially offset in opposite directions and extend through channels provided in respective structural band free ends. The fingers preferably terminate in enlarged heads that are wider than the channels. The expansion limiting spacer is preferably made of a lubricious material selected from the group consisting of polyester, polytetrafluoroethylene (PTFE), ultra-high-molecular-weight polyethylene (UHMWPE) and polyether ether ketone (PEEK).

In a second alternative embodiment, the structural band also has overlapping free ends such that relative sliding of the overlapping free ends permits expansion of the support stent, and a loop of one or more filaments is loosely threaded through holes in the structural band adjacent each free end such that slack in the loop permits the structural band to expand but prevents over-expansion of the stent past the second diameter. The loop preferably comprises a single suture threaded at least three times through the holes and tied off on the outside of the band. The slack in the loop may be located outside the band, and the loop and slack are hidden when the support stent is covered in cloth. Desirably, the overlapping free ends are located at a single one of the inflow cusps of the support stent.

In a third alternative embodiment, the valve member has an exterior fabric covering and an expansion limiting flexible loop having high tensile strength sewn to the fabric covering that permits the support stent to expand from the first diameter to the second diameter and prevents over-expansion of the stent past the second diameter. The flexible loop is desirably made of high tensile strength fiber. The flexible loop may be sewn to an outer edge of a suture-permeable sewing ring of the valve that surrounds the inflow cusps of the support stent, the sewing ring being compressible so as to permit the support stent to expand from the first diameter to the second diameter until the flexible loop becomes taut and limits further expansion. The flexible loop may be attached around the sewing ring with intermittent stitches or sewn in and out of the sewing ring with two free ends tied together. Alternatively, the flexible loop is sewn to a portion of the fabric covering directly around the support stent and incorporates a section of slack that permits the support stent to expand from the first diameter to the second diameter until the flexible loop becomes taut and limits further expansion. The structural band may have overlapping free ends such that relative sliding of the overlapping free ends permits expansion of the support stent. The overlapping free ends are desirably located at a single one of the inflow cusps of the support stent.

In any of the surgical heart valves having a structural band with overlapping free ends, a flexible sleeve may further surround the free ends and hold them radially together. In one embodiment, the sleeve is made of a material selected from the group consisting of polyester shrink wrap tubing and silicone rubber. Also, the sleeve may be biodegradable to maintain alignment of the two free ends for a period after implant and then degrade to permit even easier expansion of the band.

Any of the surgical heart valves may further include a unique identifier on the support stent visible from outside the body after implant that identifies the support stent as being expandable. The support stent for any of the heart valves may include the structural band concentrically disposed against a commissure band defining the three upstanding commissure posts of the support stent, the structural band being truncated at the commissure posts of the commissure band. The structural band is desirably made of a metal and the commissure band is desirably of a polymer.

Other features and advantages will become apparent from the following detailed description, taken in conjunction with the accompanying drawings that illustrate, by way of example, certain principles and examples.

DETAILED DESCRIPTION OF CERTAIN EMBODIMENTS

The prosthetic heart valves disclosed herein include a prosthetic valve member constructed similarly to embodiments of conventional surgical valves, with a relatively stable diameter that is not intended to be compressed or expanded during delivery and after implant when functioning as a one-way valve. The prosthetic heart valves described herein each include an internal (meaning incorporated into the valve member itself as opposed to being a supplemental element) structural stent or frame that is generally tubular in shape and that defines a flow orifice area through which blood flows from an inflow end to an outflow end. Alternatively, the shape of the internal stent can be oval, elliptical, D-shaped, irregular, or any other desired shape. The valves include flexible leaflets that selectively open and close to allow for one-way fluid flow therethrough.

Various internal stents disclosed herein have "expandable segments" that enable the stent to expand. Embodiments of the expansion can occur from the expandable segment rupturing, plastically stretching, or elastically elongating. Thus, an "expandable segment" means a location on the stent that enables it to enlarge in diameter, such as when a balloon is inflated within the stent. Examples include weak points that can rupture, thinned areas that rupture or stretch, accordion-like structures that elongate elastically or plastically, breaks in the stent that are held together with a breakable member such as a suture or spot weld, and various other means. The term, "expandable segment" thus encompasses each and every one of these alternatives, either individually or in combination.

The present application discloses specific modifications to existing surgical valves that enable manufacturers to rapidly produce a valve that accommodates valve-in-valve (ViV) procedures. Specifically, the present application contemplates retrofitting or modifying components within existing surgical valves to enable post-implant expansion, which not only converts any proven surgical valve for use in a ViV procedure, but it also reduces design and manufacturing work. Consequently, components of one popular surgical valve are described below to illustrate certain modifications thereto.

Recent publications report a drastically higher probability of annular rupture when expanding the native annulus by more than 20% by area when expanding a prosthetic heart valve therein. In light of this information, it is desirable to ensure that an expandable surgical valve expands by less than about 20% by area in some embodiments. For a 19-mm valve, a 20% increase in area corresponds to an increase in diameter of about 2 mm.

Figure 1A:
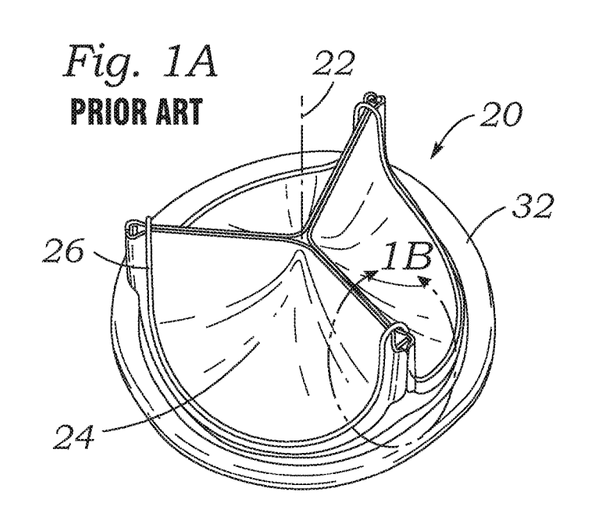
FIGS. 1A-1D are perspective and exploded views of an exemplary prosthetic heart valve of the prior art having inner structural bands.
Figure 1B:
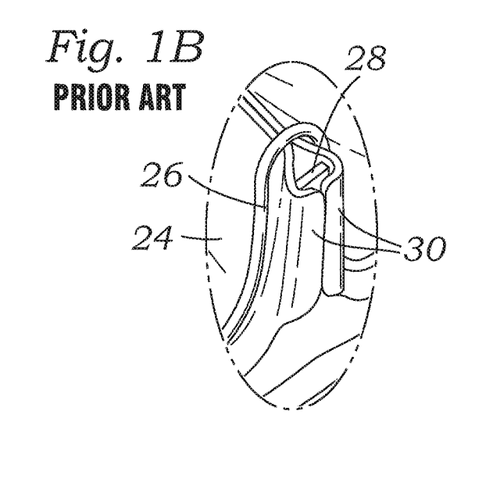

FIGS. 1A-1D are perspective and exploded views of an exemplary surgical prosthetic heart valve 20 oriented around a flow axis 22. The heart valve 20 comprises a plurality (typically three) of flexible leaflets 24 supported partly by an undulating wireform 26 as well as by a non-collapsible inner structural support stent 28. The wireform 26 and support stent 28 are visible in the figures, but are normally covered with a polyester fabric to facilitate assembly and reduce direct blood exposure after implant. The wireform 26 may be formed from a suitably elastic metal, such as a Co—Cr—Ni alloy like ELGILOY® alloy, while the support stent 28 may be metallic, plastic, or a combination of the two. As seen in FIG. 1B, outer tabs 30 of adjacent leaflets 24 wrap around a portion of the support stent 28 at so-called commissure posts of the valve that project in an outflow direction along the flow axis 22. A soft sealing or sewing ring 32 circumscribes an inflow end of the prosthetic heart valve 20 and is typically used to secure the valve to a native annulus such as using sutures.

Figure 1C:
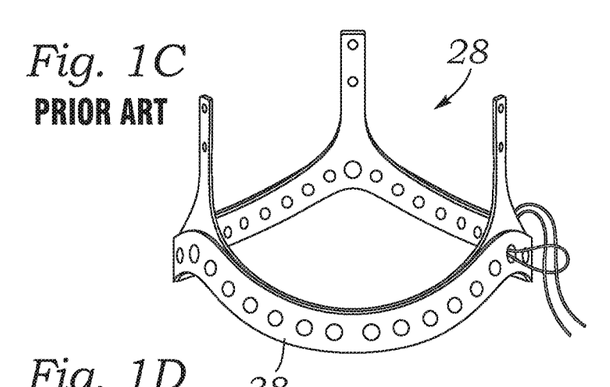
Figure 1D:
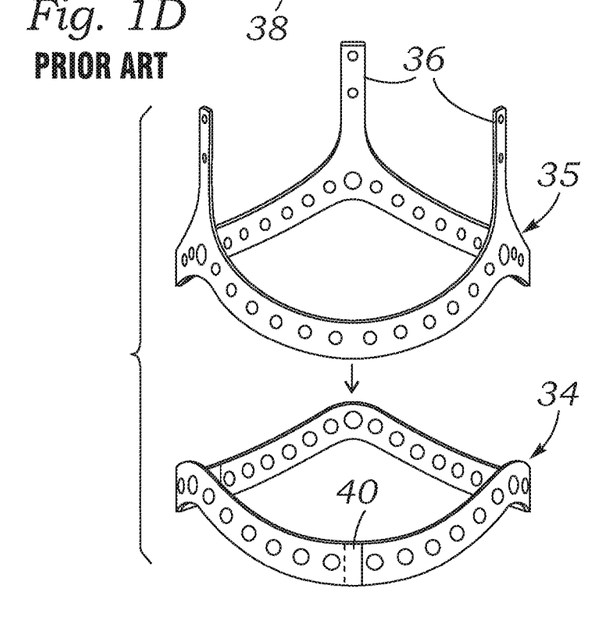

FIGS. 1C and 1D show the inner support stent 28 in both assembled and exploded views. Although the general characteristics of the prosthetic heart valve 20 as seen in FIGS. 1A and 1B may be common to a number of different prosthetic heart valves, the illustrated support stent 28 is that used in a particular heart valve; namely, pericardial heart valves manufactured by Edwards Lifesciences of Irvine, Calif. For example, the Carpentier-Edwards PERIMOUNT® heart valves that utilize pericardial leaflets 24 feature an inner stent 28 much like that shown in FIGS. 1C and 1D. In particular, the stent 28 comprises an assembly or composite of two concentric bands: an outer band 34 surrounding an inner band 35. The bands 34, 35 are relatively thin in a radial dimension as compared to an axial dimension, and both have coincident lower edges that undulate axially up and down around the circumference. The outer band 34 exhibits three truncated peaks between three downwardly curved valleys, while the inner band 35 has generally the same shape but also extends upwards at commissure posts 36. The downwardly curved valleys are typically termed cusps 38, as seen in FIG. 1C. This undulating band shape is typical for aortic heart valves, which typically have three leaflets joined at their adjacent edges at upstanding commissures. Alternatively, the structural stent may have only one band with commissure posts.

In the exemplary PERIMOUNT® valves, the outer band 34 is metallic and is formed from an elongated strip of metal closed to the generally circular shape and the ends joined together, for example, by welding, as at 40. In contrast, the in band 35 is formed of a biocompatible polymer such as polyester (e.g., polyethylene terephthalate (PET)) or polyacetal (e.g., DELRIN® polyacetal), which may be molded, and also may be formed as a strip, closed into a circular shape and the ends joined together, for example, by welding (not shown). Both the outer and inner bands 34, 35 feature a series of through holes that register with each other so that the assembly can be sewn together, as schematically illustrated in FIG. 1C at a commissure region. The wireform 26 and the commissure posts 36 of the inner band 35 provide flexibility to the commissures of the valve, which helps reduce stress on the bioprosthetic material of the leaflets 24. However, the inflow end or base of the valve 20 surrounded by the sewing ring 32 comprises the relatively rigid circular portions of the support stent 28. The combination of the metallic outer and plastic inner bands and 34, 35 presents a relatively dimensionally stable circumferential base to the valve, which is beneficial for typical surgical use. However, the same characteristics of the support stent 28 that provide good stability for the surgical valve resist post-implant expansion of the valve. Consequently, the present application contemplates a variety of modifications to the support stent 28 to facilitate expansion thereof.

The exemplary surgical valve 20 described above may thus be modified for post-implant expansion. Furthermore, a similar surgical valve structure is used in the commercial Edwards INTUITY® valve system, and the same modifications can be made in the valve component of that system so that it may be easily expanded post-implant.

Figure 2A:
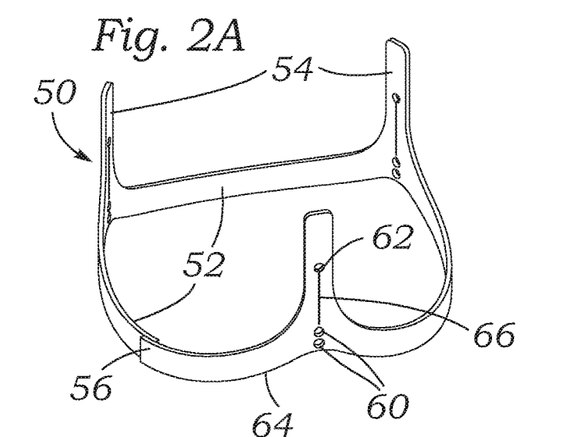
FIGS. 2A and 2B are perspective and elevational views of a first band for an exemplary combination of structural bands that can be used in various prosthetic heart valves to enable post-implantation expansion thereof.
Figure 2B:
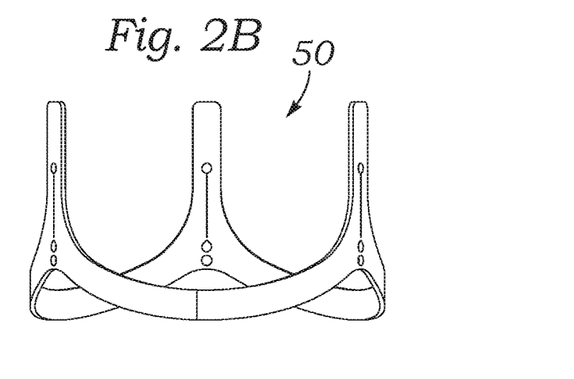

FIGS. 2A and 2B are perspective and elevational views of a first band 50 for use in an exemplary combination of structural bands to replace existing support bands and to enable post-implantation expansion thereof. The first band 50 again has a relatively small radial thickness relative to its axial height, and includes an undulating annular shape having downwardly curved cusps 52 intermediate upwardly projecting commissure posts 54. In a preferred embodiment, the first band 50 comprises a polymer material begins as a flat strip that is then curved into a circular shape and the two free ends joined together, for example, welded, as at 56.

The first band 50 includes weakened areas located below each of the commissure posts 54 that enable the band to rupture and easily expand along with the rest of the prosthetic heart valve. The first band 50 comprises a series of vertically-spaced through holes 60, 62 at each of the commissure posts 54. In particular, a first pair of through holes 60 is located closely adjacent to a lower edge 64 of the band. A vertical score line 66 through the thickness of band 50 extends vertically upwards from just above the first pair of through holes 60 to an upper through hole 62, which is located about midway up the commissure post 54. Preferably, the score line 66 connects with the upper through hole 62. The through holes 60, 62 may be circular, as shown, or may be slightly elongated such as in a teardrop shape so as to focus any tensile forces generated from expansion of the band 50 to a certain point, such as vertically upward, or may have any other suitable shape, for example, diamond, triangular, elliptical. Because of the relatively weak polymer material and the weakened areas provided by the through holes 60, 62 and score line 66, the first band 50 tends to split apart at three locations below the commissure posts 54. As explained above, the flexible leaflets are often secured to the upper ends of the commissure posts 54, which remain substantially unchanged above the upper through hole 62. Although the prosthetic heart valve in which the first band 50 is assembled is supplanted by a secondary valve, maintenance of the general integrity of the valve is desirable to avoid any loose components.

Figure 3A:
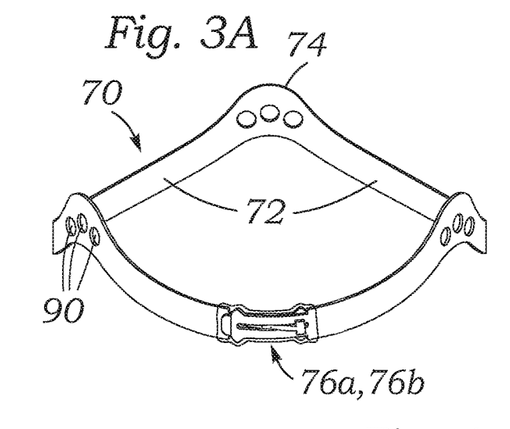
FIGS. 3A and 3B are perspective and elevational views of a second band that can be coupled with the first band of FIGS. 2A and 2B to form a combination of structural bands to be used in various prosthetic heart valve to enable post-implantation expansion thereof.
Figure 3B:
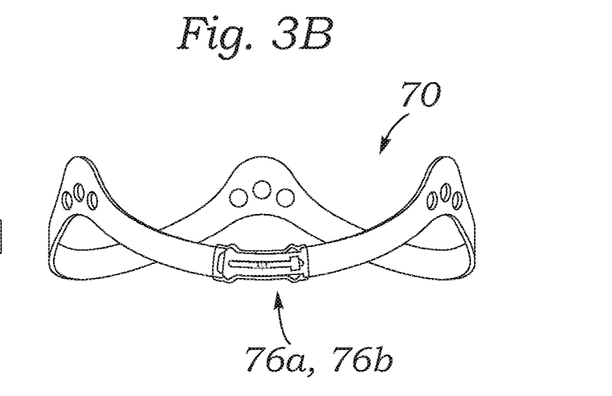
Figure 4:
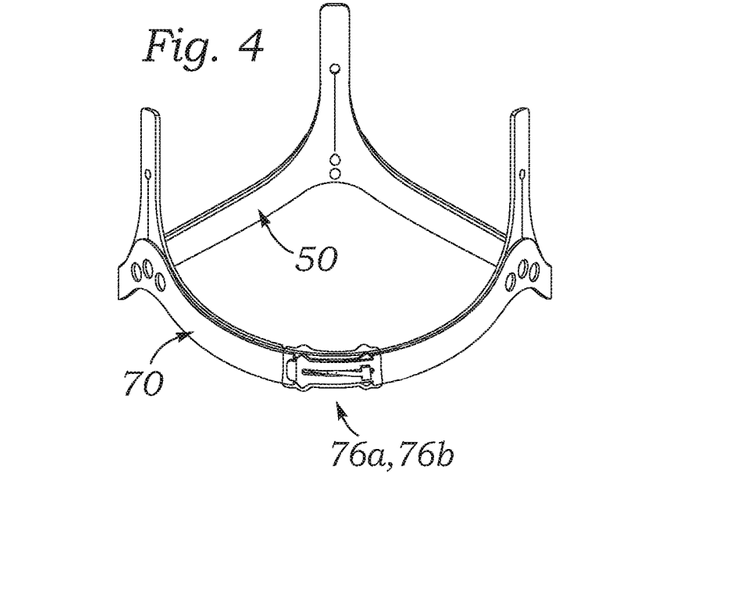
FIG. 4 is a perspective views of a combination of the structural bands in FIGS. 2 and 3 to enable post-implantation expansion of prosthetic heart valves.

FIGS. 3A and 3B are perspective and elevational views of a second band 70 that can be coupled with the first band 50 of FIGS. 2A and 2B to form a composite structural band for use in various prosthetic heart valves to enable post-implantation expansion thereof. In particular, when assembled in a heart valve, the second band 70 is concentrically located around the first band 50 in intimate contact therewith, as seen in FIG. 4. The second band 70 also has an undulating annular shape with lower-arcuate cusp regions 72 alternating with upwardly extending commissure regions 74. The two bands differ mainly in that the commissure regions 74 of the second band 70 are truncated, extending only up a portion of the commissure posts 54 of the first band 50.

The second band 70 is desirably metallic, such as a cobalt-chromium alloy, for example, a Co—Cr—Ni alloy, for example, ELGILOY® alloy (Elgiloy Specialty Metals, Elgin, Ill.), and preferably formed initially as a flat band that is circularized into an annular shape. In the illustrated embodiment, two free ends 76a, 76b of the band 70 overlap and engage each other for limited expansion. One preferred example of such engagement is shown in FIGS. 3B and 5A-5C. Because the first band 50 comprises a polymer material and the second band 70 is metallic, the second band may be termed the "structural band" inasmuch as it provide greater resistance to any dimensional changes to the support stent formed by the assembly of the two, and prosthetic valve in which the support stent is used. The first band 50 may be termed a "commissure post band" because it provides the commissure posts 54 to which the valve leaflets attach. It should also be understood that these two concentric bands may be combined into one structural band with commissure posts, and the two free ends desirably provided at a cusp region.

Figure 5A:
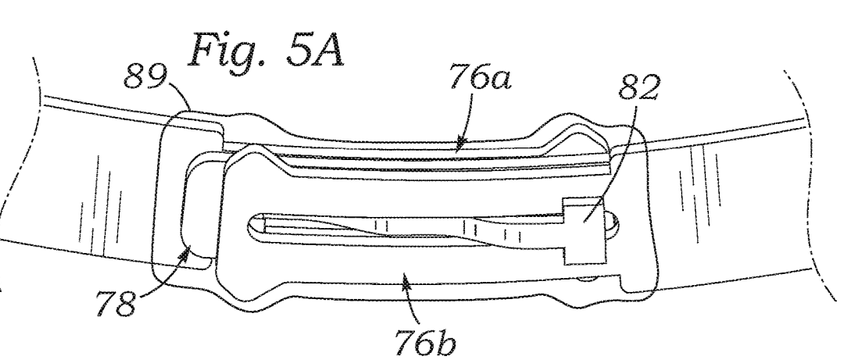
FIGS. 5A-5C are unexpanded, expanded and top plan views of an exemplary heart valve band configuration with limited expansion capacity.
Figure 5B:
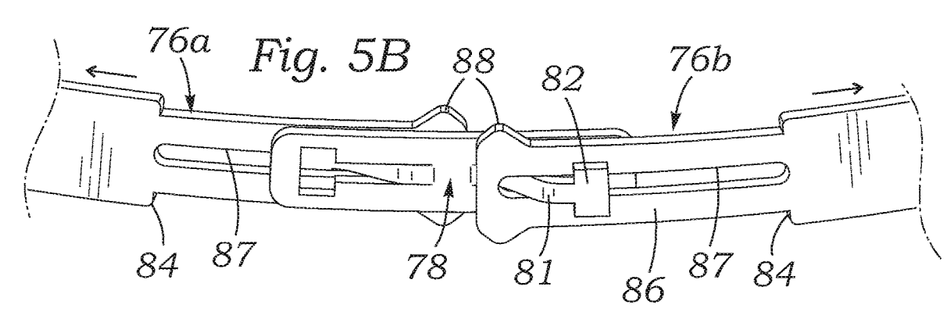
Figure 5C:
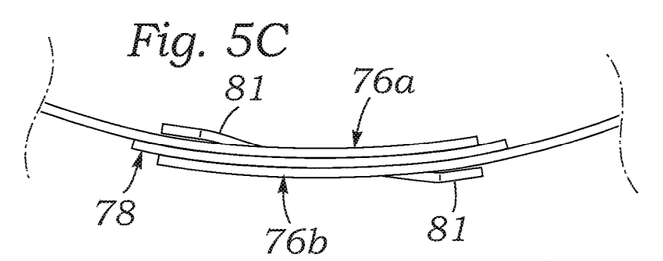
Figure 6A:
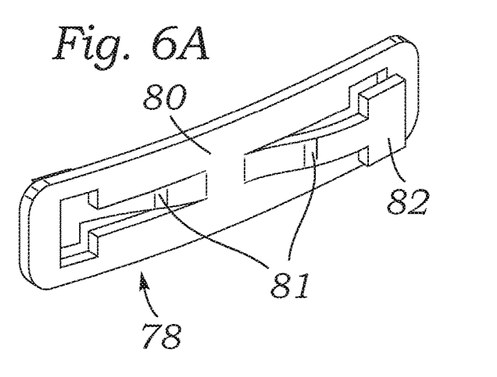
FIGS. 6A-6C are perspective and orthogonal views of an exemplary locking tabs for use in the band configuration of FIGS. 5A-5C.
Figure 6B:
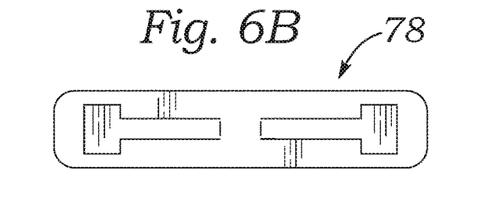
Figure 6C:
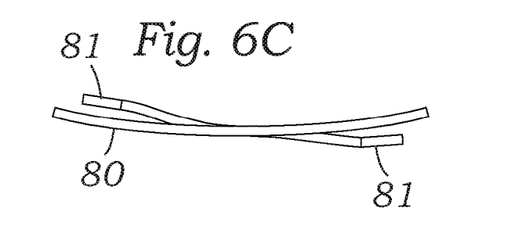

As seen in FIGS. 5A-5C, the two free ends 76a, 76b in this example are radially separated by a sliding insert or "spacer" 78, shown in more detail in FIG. 6A-6C. For example, the spacer 78 is formed of a lubricious material such as polyester, polytetrafluoroethylene (PTFE), ultra-high-molecular-weight polyethylene (UHMWPE). The spacer 78 is primarily formed as a radially thin rectangular body 80 that has a curvature the same as or similar to the curvatures of the two free ends 76a, 76b. A pair of offset interlocking fingers 81 having enlarged tabs 82 are cut from and project on either radial side of the body 80, as see in FIGS. 6A and 6C. The fingers 81 commence near the middle of the body 80, project away from each other and are angled radially away from opposite sides of the body. Each finger 81 is generally rectangular and terminates in the enlarged tabs 82, which is also illustrated as rectangular. The spacer 78 is desirably made from about 0.1 mm (about 0.004") thick polyester (e.g., PET) and is die-cut, or could be cut or molded from other, stronger materials if needed, such as polyether ether ketone (PEEK). The spacer can also be a composite, for example, including a stronger central layer and lubricious outer layers.

The two free ends 76a, 76b are each distinguished from the rest of the band at a pair of shoulders 84 that reduce the axial height of an intermediate portion 86 having a central circumferential slot 87. Each free end 76a, 76b terminates in an axially enlarged head 88 (or oppositely-directed axial bumps) having an axial height that is approximately the same as the majority of the band 70, or the same as the two non-expandable cusp regions of the band. The fingers 81 on the sliding spacer 78 extend through the circumferential slots 87 on respective free ends 76a, 76b, as best see in FIGS. 5B and 5C.

The assembly of the two free ends 76a, 76b and spacer 78 seen in FIG. 5A is held together by a flexible sleeve 89 which surrounds the free ends 76a, 76b and holds them radially together. The sleeve 89 desirably comprises polyester (e.g., PET) shrink wrap tubing, or may be an elastic material, such as silicone rubber, and is shown transparent to illustrate the mating free ends 76a, 76b. The two free ends 76a, 76b may slide apart a predetermined distance while remaining overlapping. The flexible sleeve 89 provides a small or minimum amount of friction against the axially enlarged heads 88, and generally serves to maintain alignment of the free ends 76a, 76b.

The assembly of the first band 50 in intimate contact with the second band 70, as seen in FIG. 4, provides good stability for the prosthetic valve leaflets when in use, and an advantageous expandable structure if and when a valve-in-valve procedure is necessary. The flexible sleeve 89 nominally maintains the diameter of the band so that it is stable during manufacturing, but allows it to easily open up or expand when a valve-in-valve procedure is performed. Moreover, the sleeve 89 may be biodegradable to maintain alignment of the two free ends 76a, 76b for a period after implant and then degrade to permit even easier expansion of the band 70 when desired.

When a dilatory force such as an expanding balloon is applied within the heart valve, the free ends 76a, 76b slide apart and one or more of the weakened areas on the first band 50 located below each of the commissure posts 54 rupture so that the main circular support for the valve expands. The wireform 26 or other structure of the valve easily flexes apart. The preferably metal outer band 70 only expands at one location, while the preferably polymer band 50 can expand at all three commissures. The outer band 70 is able to slide within the surrounding cloth coverings and relative to the other components such that the valve expands generally uniformly around its perimeter. That is, the commissure areas of a wireform to which the leaflets attach and commissure areas of the metal band 70 are initially aligned, or registered. As the metal band 70 expands, the registered commissure areas become misaligned since the wireform 26 expands at all three commissures and the metal band only expands at the one cusp. However, the valve becomes obsolete, having been replaced with a transcatheter valve, and so this misalignment is of no consequence. The wireform maintains the upstanding commissure posts of the expanded valve in roughly the same locations as when they were functional, which are intermediate the surrounding coronary ostia, and thus valve expansion will not end up blocking critical blood flow to the coronary arteries.

Interference between the interlocking fingers 81 on the sliding spacer 78 and the circumferential slots 87 on the free ends 76a, 76b limits total expansion of the band 70. FIG. 5A shows the band in its unexpanded configuration with the free ends 76a, 76b nearly completely overlapping. FIG. 5B shows the free ends 76a, 76b separating, such as if a dilating device, for example, a balloon, expands within the prosthetic heart valve in a ViV procedure. Each of the enlarged tabs 82 on the fingers 81 remains on a respective side of the associated circumferential slot 87, ultimately preventing the free ends 76a, 76b from separating completely. As such, the sliding spacer limits total expansion of the band 70, such as to a pre-determined amount, about 2 mm for example. The geometry of the interlocking fingers 81 and slots 87 may be dimensioned to limit expansion of the band 70, and valve, to one or two valve sizes, for example, with 2 mm between each valve size.

The particular configuration of the sliding spacer 78 with fingers 81 that interlock with both free ends 76a, 76b is exemplary only and may take other forms. For example, the enlarged tabs 82 may be shaped differently such as being square or rounded rather than rectangular. Further, the sliding spacer 78 may be eliminated in favor of interlocking elements on the respective free ends 76a, 76b. In some examples in which the band is metallic, the polymer spacer 78 reduces sliding friction and/or possible detrimental sloughing of material that may result from metal-on-metal contact. Still further, alternative constructions for limiting expansion of the internal valve structure are shown and described below.

It should also be noted that although there is preferably a single point of expansion at the free ends 76a, 76b at one of the cusp regions of the band 70, as shown, the two non-expandable cusp regions of the band may also have similar points of expansion. In that instance, the overall magnitude of expansion at each cusp region will be less than needed for a single point of expansion, such as one third of the desirable increase in diameter of 2 mm. Further, providing three points of expansion will help reduce any misalignment of the existing valve commissures that may occur from expanding at only one cusp.

The band 70 preferably includes an identifying trait visible using external imaging and signifying it is expandable. In the embodiment illustrated in FIG. 4, a pattern of three holes 90 is provided at each commissure region 74. Again, this permits a surgeon contemplating a replacement operation to quickly confirm that a valve-in-valve procedure is a possibility. The band 70 may also include a valve size indicator visible using external imaging, such as having a valve size number, for example, a valve size in millimeters, laser cut though the band.

Figure 7A:
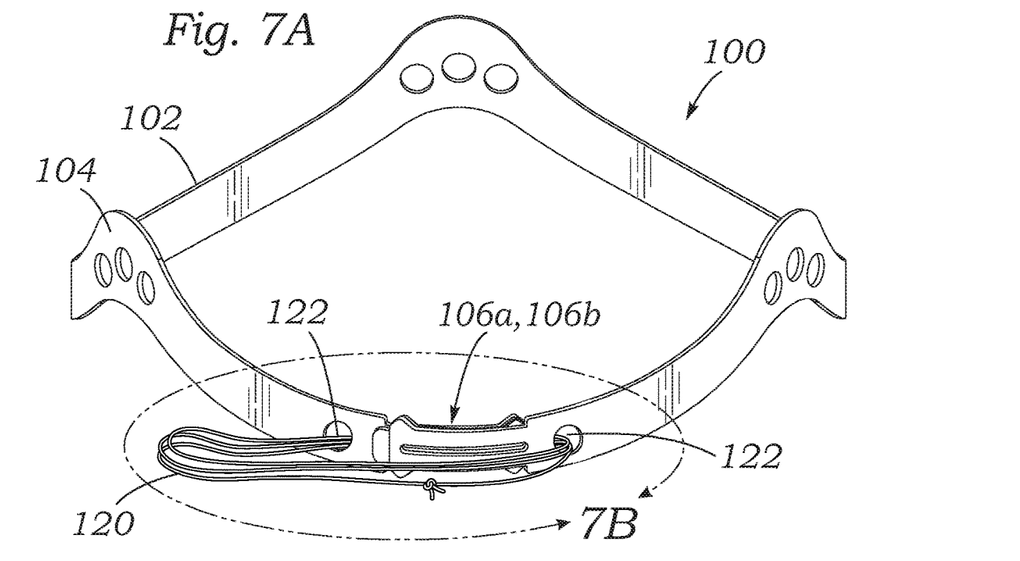
FIG. 7A is a perspective view of a further band with limited expansion capacity for use in heart valves.
Figure 7B:
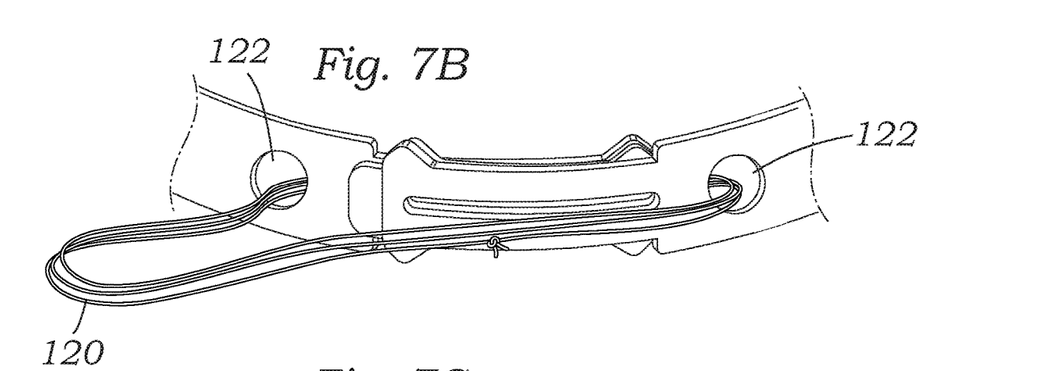
FIGS. 7B and 7C are enlarged views of overlapping free ends of the band in unexpanded and expanded states.

Another concept for limiting the expansion of prosthetic heart valves is shown in FIG. 7A. Specifically, a stent including a structural band 100 is shown, which is much like the band 70 of FIG. 3A and which is shaped to mate with a secondary band having commissure posts, such as band 50 of FIG. 2A. Alternatively, the structural band 100 may feature commissures and be shaped to function as a stent on its own. As before, the structural band 100 includes three cusps 102 between three commissures 104 in an undulating pattern which is conventional for aortic heart valves.

The band 100 is contiguous except at two overlapping free ends 106a, 106b located at about the middle of one of the cusps 102. As before, the free ends 106a, 106b are adapted to slide with respect to one another and thus permit expansion of the stent upon application of an outward dilatory force such as in a ViV procedure. In the illustrated embodiment, the two free ends 106a, 106b are shaped somewhat like the free ends 76 described above. A sliding insert or "spacer" 112 is interposed between the two free ends 106a, 106b to reduce sliding friction therebetween. For example, the spacer 112 is formed of a lubricious material such as polyester, PTFE, or UHMWPE. The assembly of the two free ends 106a, 106b and spacer 112 may be held together by a flexible sleeve (not illustrated), which surrounds the free ends 106a, 106b and holds them radially together, such as was described above with respect to the sleeve 89. The flexible sleeve also provides a small or minimum amount of friction against the free ends 106a, 106b.

Figure 7C:
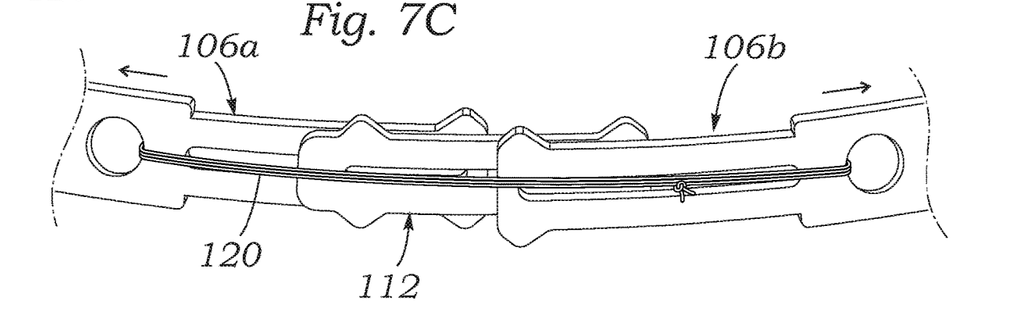

Expansion of the band 100 is limited by a loop 120 of one or more filaments loosely threaded through holes 122 in the band 100 adjacent each free end 106a, 106b. The loop 120 may comprise a suture or any other flexible biocompatible member. In the illustrated embodiment the loop 120 is formed by a single suture threaded three times through the holes 122 and tied off on the outside of the band. A certain amount of slack in the loop 120 permits the band 100 to expand in a ViV procedure, for example, but expansion is limited thereby. The loop 120 is hidden when the assembly is covered in cloth, and its slack would preferably be located outside the band 100. Upon expansion of the heart valve, the loop 120 becomes taut at a predetermined diameter of the band 100 to prevent further expansion, as shown in FIG. 7C. For example, the loop 120 may be dimensioned to limit expansion of the band 100, and valve, to about 2 mm, or about one valve size.

Although the preceding configurations for limiting expansion of prosthetic heart valves by one or two sizes have been successfully tested, each require modification to a design of an already expandable valve. FIGS. 8-11 illustrate still further variations for limiting valve expansion that do not require significant modification of existing valves by introducing exterior loops of filament that can be easily sewn into the fabric covering the valves.

Figure 8:
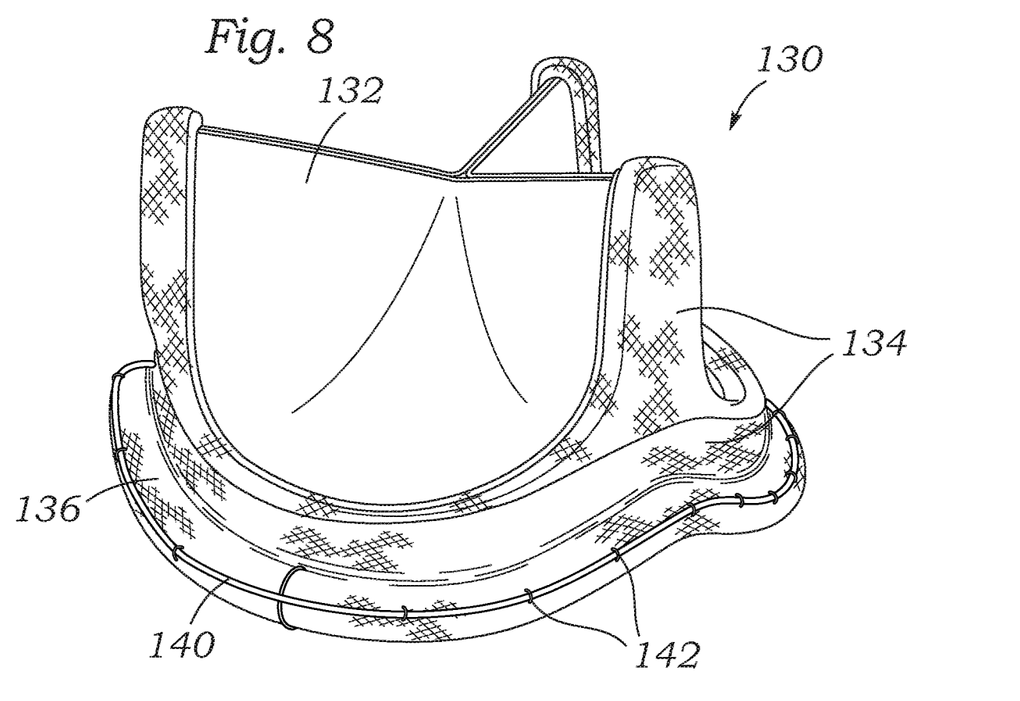
FIGS. 8-10 are perspective views of a prosthetic heart valve having a peripheral suture for limiting overall expansion of the valve.

FIG. 8 shows a typical heart valve 130 much as described above having three flexible leaflets 132 supported by an internal stent structure (not shown) covered in biocompatible fabric 134. In the illustrated embodiment the valve 130 has a sewing ring 136 disposed circumferentially about an inflow end thereof. A loop 140 of flexible material such as a suture is added around the sewing ring 136 to limit the ability of the valve to expand. More particularly, the loop 140 is attached around the sewing ring 136 with intermittent stitches 142. The loop 140 may be made of high tensile strength fiber (e.g., DYNEEMA® UHMWPE, SPECTRA® UHMWPE, or KEVLAR® aramid), and is flexible so that it follows the scalloped-shape contour and is placed at a distance away from or spaced from the inner surface of the sewing ring 136. The distance from the inner surface of the sewing ring 136 permits some compression of the sewing ring from valve expansion but ultimately limits the amount of expansion and defines the final expanded diameter.

It should be understood that expansion-limiting solutions utilizing loops of material attached (e.g., sewn) to the exterior of the heart valve can be implemented across various expandable surgical valve designs, since it is independent of the internal structure of the valve. That is, the heart valves disclosed herein may be utilized without a secondary expansion-limiting solution within the valve structure, or any other expandable valve such as disclosed in U.S. Pat. Nos. 8,613,765, 9,314,335, 9,364,322, 9,375,310, and International Patent Publication No. WO 2012/018779, the disclosures of which are expressly incorporated herein by reference.

Figure 9:
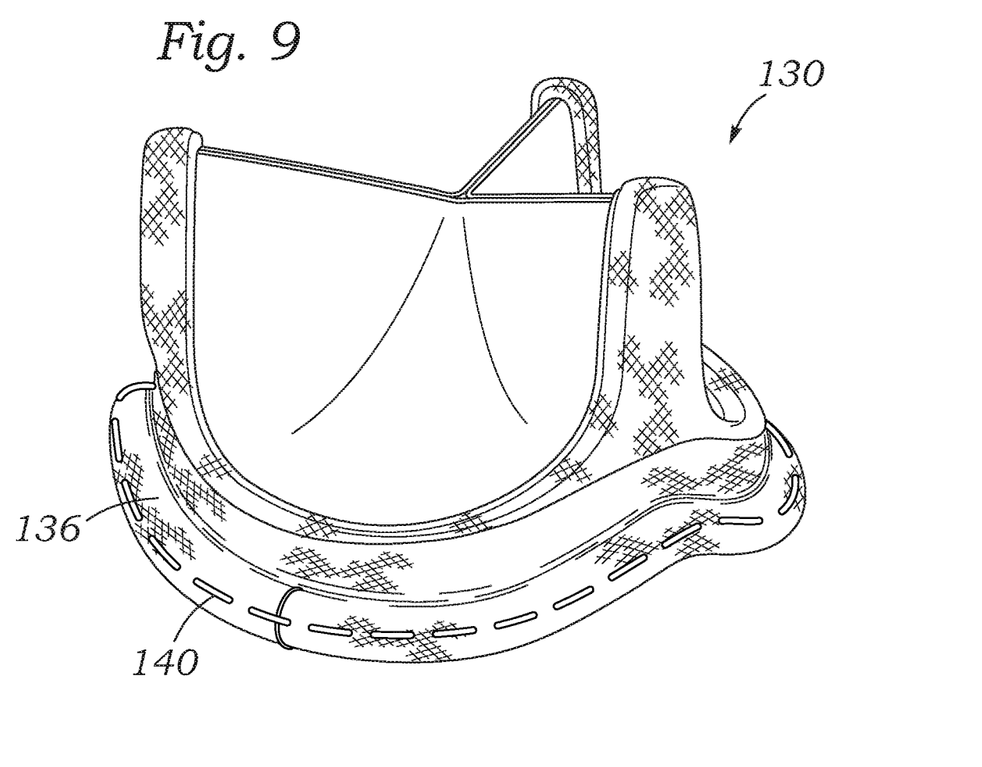

The loop 140 can be constructed as a separate piece and attached/sewn to the sewing ring 136. Alternatively, the loop 140 can be constructed by sewing the high tensile strength fiber in and out of the sewing ring 136 and tying the ends together, such as shown in FIG. 9. The loop 140 is completed when the free ends of the high tensile strength fiber are tied in a knot or crimped. In some examples, the loop 140 is a separately manufactured closed loop that does not require knotting or crimping during assembly of the prosthetic valve, which facilitates uniform sizing and/or simplified manufacturing.

Figure 10:
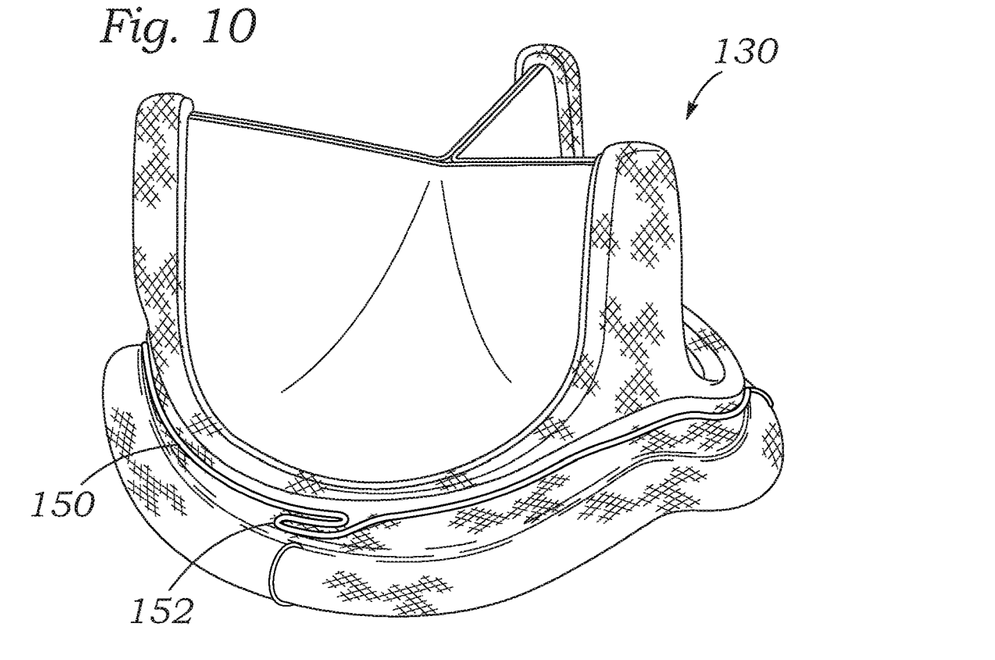

FIG. 10 shows another version of a loop 150 for limiting expansion of the heart valve 130. In this version, the loop 150 attaches around an upper portion of the fabric-covered internal stent, described above, and includes built-in relief or slack 152 that permits expansion of the valve. At a certain diameter of the stent, the slack 152 tightens and limits further expansion (to one or more valve sizes).

Figure 11:
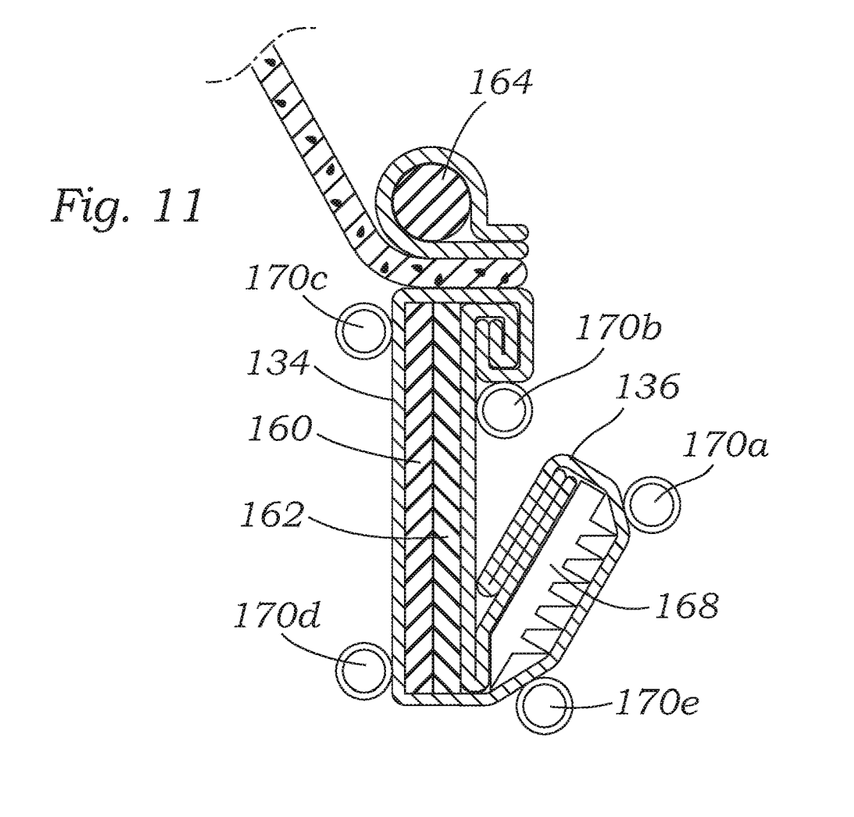
FIG. 11 is a radial sectional view through a cusp edge of a prosthetic heart valve such as in FIGS. 8-10 showing various locations for placing an expansion limiting suture.

FIG. 11 shows a radial cross section of the valve 130 with potential locations of placement of the expansion-limiting loops described above. The valve 130 includes an internal stent with an inner band 160 and an outer band 162, and a wireform 164. The outer edges 166 of the leaflets 132 are secured between the upper end of the fabric-covered composite bands 160, 162 and wireform 164. The sewing ring 136 is shown attached at its inner surface to the outer band 162 and includes a suture-permeable insert 168, such as silicone rubber. The locations of possible placement of the expansion-limiting loops are given at 170a-170e. Depending on the placement, a length of slack may be included in the loop, such as shown at 152 in FIG. 10.

The specific locations shown are: on the outer edge of the sewing ring 136 at 170a, on an outer edge of the stent (composite bands 160, 162) at 170b, to the inside of the stent at 170c, at an inflow end of the stent at 170d (inside the stent), and at the underside of the sewing ring 136 at 170e. Each of these locations has a fabric covering such as at 134, and so the loop of suture material can either be stitched in and out of the fabric or supplemental stitches added to hold it in place.

Again, this particular expansion-limiting solution can be implemented across various expandable surgical valve designs, since it is independent of and therefore avoids modification to the internal structure of the valve. This approach also could allow tailored amount of expansion that could be independent of the design of the internal structure of the valve While certain principles have been described with reference to particular embodiments, it will understood that various changes and additional variations may be made and equivalents may be substituted for elements thereof without departing from the scope of the disclosure. In addition, many modifications may be made to adapt a particular situation or device to the teachings without departing from the essential scope thereof. Therefore, it is intended that the disclosure not be limited to the particular embodiments disclosed herein, but will include all embodiments falling within the scope of the appended claims.

What is claimed is:

1. A prosthetic surgical heart valve adapted for post-implant expansion and having an inflow end and an outflow end, comprising:
a valve member including a non-collapsible inner structural support stent supporting leaflets configured to ensure one-way blood flow through the valve member, a periphery of the support stent defining a non-collapsible delivery and implant circumference having a first diameter, wherein the support stent is configured to permit expansion of the periphery beyond the first diameter upon application of an outward dilatory force from within the support stent substantially larger than forces associated with normal physiological use, and further including an expansion limiting loop of flexible material attached around the valve member having built-in relief or slack that permits expansion of the support stent from the first diameter to a second diameter larger than the first diameter but which defines a maximum circumference that limits expansion of the support stent to the second diameter, wherein the valve member includes a compressible suture-permeable sewing ring disposed circumferentially about an inflow end of the support stent, and the loop attaches to an underside of the sewing ring.

2. The prosthetic heart valve of claim 1, wherein the support stent is covered with fabric and the loop attaches around an upper portion of the fabric-covered support stent.

3. The prosthetic heart valve of claim 1, wherein the support stent is covered with fabric and the loop attaches to the inside of the fabric-covered support stent.

4. The prosthetic heart valve of claim 3, wherein the loop attaches to an inflow end of the stent.

5. The prosthetic heart valve of claim 1, wherein the loop is made of high tensile strength fiber.

6. The prosthetic heart valve of claim 1, wherein the loop is attached around the sewing ring with intermittent stitches.

7. The prosthetic heart valve of claim 1, further including a unique identifier on the support stent visible from outside the body after implant that identifies the support stent as being expandable.

8. The prosthetic heart valve of claim 1, wherein the support stent includes expansion limiting structure that permits expansion of the support stent from the first diameter to a larger diameter and limits expansion of the support stent to the larger diameter.

9. The prosthetic heart valve of claim 8, wherein the larger diameter is equal to the second diameter.

10. The prosthetic heart valve of claim 1, wherein the support stent includes a structural band extending around the periphery and having overlapping free ends such that relative sliding of the overlapping free ends permits expansion of the support stent from the first diameter to a larger diameter, and further including an expansion limiting spacer interposed between the overlapping free ends that limits expansion of the support stent to the larger diameter.

11. A prosthetic surgical heart valve adapted for post-implant expansion and having an inflow end and an outflow end, comprising:
a valve member including a non-collapsible inner structural support stent supporting leaflets configured to ensure one-way blood flow through the valve member and a compressible suture-permeable sewing ring disposed circumferentially about an inflow end of the support stent, a periphery of the support stent defining a non-collapsible delivery and implant circumference having a first diameter, wherein the support stent is configured to permit expansion of the periphery beyond the first diameter upon application of an outward dilatory force from within the support stent substantially larger than forces associated with normal physiological use, and further including an expansion limiting loop of flexible material made of high tensile strength fiber attached around the sewing ring that permits expansion of the support stent from the first diameter to a second diameter larger than the first diameter by outward compression of the sewing ring but which becomes taut to define a maximum circumference that limits expansion of the support stent to the second diameter.

12. The prosthetic heart valve of claim 11, wherein the loop is attached around the sewing ring with intermittent stitches.

13. The prosthetic heart valve of claim 11, wherein the flexible material is sewn in and out around the sewing ring and with ends of the flexible material tied together or crimped to form the loop.

14. The prosthetic heart valve of claim 11, wherein the loop attaches to an outer edge of the sewing ring.

15. The prosthetic heart valve of claim 11, further including a unique identifier on the support stent visible from outside the body after implant that identifies the support stent as being expandable.

16. The prosthetic heart valve of claim 11, wherein the support stent includes expansion limiting structure that permits expansion of the support stent from the first diameter to a larger diameter and limits expansion of the support stent to the larger diameter.

17. The prosthetic heart valve of claim 16, wherein the larger diameter is equal to the second diameter.

18. The prosthetic heart valve of claim 11, wherein the support stent includes a structural band extending around the periphery and having overlapping free ends such that relative sliding of the overlapping free ends permits expansion of the support stent from the first diameter to a larger diameter, and further including an expansion limiting spacer interposed between the overlapping free ends that limits expansion of the support stent to the larger diameter.

19. The prosthetic heart valve of claim 18, wherein the expansion limiting spacer is made of a lubricious material selected from the group consisting of polyester, polytetrafluoroethylene (PTFE), ultra-high-molecular-weight polyethylene (UHMWPE) and polyether ether ketone (PEEK).

20. A prosthetic surgical heart valve adapted for post-implant expansion and having an inflow end and an outflow end, comprising:

a valve member including a non-collapsible inner structural support stent supporting leaflets configured to ensure one-way blood flow through the valve member and a compressible suture-permeable sewing ring disposed circumferentially about an inflow end of the support stent, a periphery of the support stent defining a non-collapsible delivery and implant circumference having a first diameter, wherein the support stent is configured to permit expansion of the periphery beyond the first diameter upon application of an outward dilatory force from within the support stent substantially larger than forces associated with normal physiological use, and further including an expansion limiting loop of flexible material attached around the sewing ring that permits expansion of the support stent from the first diameter to a second diameter larger than the first diameter by outward compression of the sewing ring but which becomes taut to define a maximum circumference that limits expansion of the support stent to the second diameter, wherein the loop is attached around the sewing ring with intermittent stitches.

21. A prosthetic surgical heart valve adapted for post-implant expansion and having an inflow end and an outflow end, comprising:

a valve member including a non-collapsible inner structural support stent supporting leaflets configured to ensure one-way blood flow through the valve member and a compressible suture-permeable sewing ring disposed circumferentially about an inflow end of the support stent, a periphery of the support stent defining a non-collapsible delivery and implant circumference having a first diameter, wherein the support stent is configured to permit expansion of the periphery beyond the first diameter upon application of an outward dilatory force from within the support stent substantially larger than forces associated with normal physiological use, and further including an expansion limiting loop of flexible material attached around the sewing ring that permits expansion of the support stent from the first diameter to a second diameter larger than the first diameter by outward compression of the sewing ring but which becomes taut to define a maximum circumference that limits expansion of the support stent to the second diameter, wherein the flexible material is sewn in and out around the sewing ring and with ends of the flexible material tied together or crimped to form the loop.

* * * * *